United States Patent
Zhang et al.

(10) Patent No.: US 11,156,689 B2
(45) Date of Patent: Oct. 26, 2021

(54) RESPIRATORY NAVIGATION SIGNAL EXTRACTION METHOD AND APPARATUS, MAGNETIC RESONANCE IMAGING SYSTEM AND STORAGE MEDIUM

(71) Applicant: Siemens Healthcare GmbH, Erlangen (DE)

(72) Inventors: Qiong Zhang, Shenzhen (CN); Wei Liu, Shenzhen (CN); Nan Xiao, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/851,609

(22) Filed: Apr. 17, 2020

(65) Prior Publication Data
US 2020/0333419 A1  Oct. 22, 2020

(30) Foreign Application Priority Data
Apr. 19, 2019  (CN) .......................... 201910317802.8

(51) Int. Cl.
*G01R 33/567* (2006.01)
*G01R 33/54* (2006.01)
*A61B 5/00* (2006.01)
*A61B 5/055* (2006.01)
*A61B 5/113* (2006.01)

(52) U.S. Cl.
CPC .......... *G01R 33/5676* (2013.01); *A61B 5/055* (2013.01); *A61B 5/7207* (2013.01); *A61B 5/7278* (2013.01); *G01R 33/543* (2013.01); *A61B 5/113* (2013.01)

(58) Field of Classification Search
CPC ............. G01R 33/5676; G01R 33/543; A61B 5/7207; A61B 5/7278; A61B 5/055; A61B 5/113
See application file for complete search history.

(56) References Cited

U.S. PATENT DOCUMENTS

| | | | | |
|---|---|---|---|---|
| 6,181,832 B1* | 1/2001 | Maas, III | ................. | G06K 9/03 |
| | | | | 382/275 |
| 7,394,251 B2* | 7/2008 | Lin | .................... | G01R 33/4824 |
| | | | | 324/309 |
| 7,570,054 B1* | 8/2009 | Lin | ................... | G01R 33/34084 |
| | | | | 324/307 |
| 7,576,536 B2* | 8/2009 | Akao | ................. | G01R 33/5611 |
| | | | | 324/307 |
| 8,581,589 B2* | 11/2013 | Wald | ................... | G01R 33/3621 |
| | | | | 324/322 |
| 10,429,475 B2* | 10/2019 | Polimeni | ............ | G01R 33/5608 |
| 2008/0012564 A1* | 1/2008 | Lin | .................... | G01R 33/4824 |
| | | | | 324/309 |

(Continued)

OTHER PUBLICATIONS

Speier, P. et al. "PT-Nav: A Novel Respiratory Navigation Method for Continuous Acquisition Based on Modulation of a Pilot Tone in the MR-Receiver" ESMRMB 129:97-98, 2015. doi: 10.1007/s10334-015-0487-2.

*Primary Examiner* — Dixomara Vargas
(74) *Attorney, Agent, or Firm* — Schiff Hardin LLP

(57) ABSTRACT

The present disclosure related to techniques for extracting a respiratory navigation signal for use in a magnetic resonance imaging system. The extracted respiratory navigation signals accurately represent respiratory motions of a patient.

11 Claims, 9 Drawing Sheets

(56) References Cited

U.S. PATENT DOCUMENTS

| | | | | |
|---|---|---|---|---|
| 2009/0179643 A1* | 7/2009 | Lin | ............... | G01R 33/5611 |
| | | | | 324/312 |
| 2010/0289494 A1* | 11/2010 | Wald | ............... | G01R 33/3621 |
| | | | | 324/318 |
| 2015/0374237 A1* | 12/2015 | Hu | ............... | A61B 5/7285 |
| | | | | 600/413 |
| 2016/0003928 A1* | 1/2016 | Chen | ............... | G01R 33/4822 |
| | | | | 324/309 |
| 2016/0025833 A1* | 1/2016 | Polimeni | ............... | G01R 33/5608 |
| | | | | 324/309 |
| 2019/0142528 A1* | 5/2019 | Vertikov | ............... | A61B 8/488 |
| | | | | 600/424 |
| 2020/0341102 A1* | 10/2020 | Eck | ............... | G01R 33/54 |
| 2020/0375463 A1* | 12/2020 | Hess | ............... | A61B 5/7289 |

* cited by examiner

1

RESPIRATORY NAVIGATION SIGNAL EXTRACTION METHOD AND APPARATUS, MAGNETIC RESONANCE IMAGING SYSTEM AND STORAGE MEDIUM

CROSS-REFERENCE TO RELATED APPLICATIONS

The present application claims the benefit of the filing date of China patent application no. 201910317802.8, filed on Apr. 19, 2019, the contents of which are incorporated herein by reference in their entirety.

TECHNICAL FIELD

The present disclosure relates to magnetic resonance imaging, and in particular to techniques for extracting a respiratory navigation signal.

BACKGROUND

Magnetic resonance imaging (MRI) is a technique using magnetic resonance phenomena for imaging. The principle of magnetic resonance imaging mainly involves nuclei containing an odd number of proton(s), for example, hydrogen nuclei widely existing in a human body. The protons thereof are in a spin motion, like small magnets, and the small magnets have irregular axes of spin. If an external magnetic field is applied, the small magnets will be rearranged according to magnetic force lines of the external magnetic field, and are specifically arranged in two directions, i.e. directions parallel to and anti-parallel to the magnetic force lines of the external magnetic field. The direction parallel to the magnetic force lines of the external magnetic field mentioned above is referred to as a positive longitudinal axis, and the direction anti-parallel to the magnetic force lines of the external magnetic field mentioned above is referred to as a negative longitudinal axis. The nuclei have a longitudinal magnetization component that has both direction and amplitude. Nuclei in the external magnetic field are excited by radio frequency (RF) pulses at a specific frequency such that the axes of spin of the nuclei deviate from the positive longitudinal axis or the negative longitudinal axis so as to produce resonance, which is the magnetic resonance phenomenon. After the axes of spin of the excited nuclei mentioned above deviate from the positive longitudinal axis or the negative longitudinal axis, the nuclei have a transverse magnetization component.

After transmitting radio frequency pulses, the excited nuclei transmit echo signals gradually release the absorbed energy in the form of electromagnetic waves, have both the phase and energy level thereof being restored to the state before being excited, and the echo signals transmitted by the nuclei are subjected to further processing such as space encoding such that the image can be reconstructed.

In the magnetic resonance imaging process, imaging is distorted by respiratory motions, and the effect thereof is obvious, especially when abdominal magnetic resonance imaging is performed. Therefore, sometimes there is a need to perform navigation for a scanning process according to respiratory signals in the imaging process. For example, respiratory signals of a patient are detected by means of an abdominal pressure detection apparatus tied to the abdomen. Magnetic resonance imaging sequence and signal collection is triggered or gated in a plateau phase of the patient inhaling or exhaling, and high-quality images can only be obtained when the respiratory wave is accurately controlled. The respiratory signal may be referred to as a magnetic resonance imaging navigation signal.

Currently, there is a pilot tone navigator that can provide respiratory signals for a continuous sequence with minimal hardware requirements, which is comparable to the "gold standard" magnetic resonance navigator. As shown in FIG. 1A, purely respiration-modulated pilot tone (PT) signals received on six channels are shown. However, in some cases, when an MRI sequence of RF pulses are run, the received pilot tone signals are severely distorted, and as shown in FIG. 1B, distorted PT signals (i.e., disturbed or noisy PT signals) received on six channels when a sequence of RF pulses are triggered to run are shown. It can be seen that the distorted signals can no longer accurately represent respiratory motions, and therefore the pilot tone navigator cannot be considered as a respiratory navigator.

SUMMARY

In view of this, one embodiment of the present disclosure proposes a respiratory navigation signal extraction method and apparatus, and another embodiment thereof proposes a magnetic resonance imaging system and a computer readable storage medium to process signals received on the pilot tone navigator, and reproduce respiratory signals that can accurately represent respiratory motions, so as to further enable the pilot tone navigator to be used as a respiratory navigator.

The respiratory navigation signal extraction method provided in the embodiments of the present disclosure comprises: acquiring purely respiration-modulated pilot tone signals of a first predetermined number of points that are received on a plurality of channels before a sequence of RF pulses run; performing eigenvalue decomposition on the pilot tone signals on the plurality of channels based on a covariance matrix and determining, as a respiratory feature direction, the direction of an eigenvector with the strongest energy; acquiring distorted pilot tone signals of a second predetermined number of points that are received on the plurality of channels and generating signal transients when a sequence of RF pulses run; performing eigenvalue decomposition on the distorted pilot tone signals on the plurality of channels based on the covariance matrix to obtain an eigenvector matrix and determining, as a distorted feature direction, the direction of an eigenvector with the strongest energy; performing, by using the eigenvector matrix, orthogonal transformation for each of the pilot tone signals received on the plurality of channels, respectively, to obtain a plurality of signals corresponding to the directions of various eigenvectors; and performing, in the respiratory feature direction, projection and addition of signals in eigenvector directions other than that of a signal in the distorted feature direction to obtain a respiratory navigation signal.

In one implementation, said acquiring distorted pilot tone signals of a second predetermined number of points that are received on the plurality of channels and generating signal transients when a sequence of RF pulses run comprises acquiring distorted pilot tone signals of the second predetermined number of points that are received on the plurality of channels and generating signal transients when the sequence of RF pulses run for a first cycle.

In one implementation, the respiratory navigation signal extraction method further comprises: acquiring, for each currently obtained experimental value, purely respiration-modulated pilot tone signals of points with the number being the experimental value that are received on the plurality of channels, performing eigenvalue decomposition on the pilot tone signals on the plurality of channels based on the covariance matrix and determining, as a respiratory feature direction, the direction of an eigenvector with the strongest energy, calculating an angle between the respiratory feature direction and a fixed vector direction, and determining, as the first predetermined number, a minimum experimental value that enables the angle to be stable.

In one implementation, said acquiring, for each currently obtained experimental value, purely respiration-modulated pilot tone signals of points with the number being the experimental value that are received on the plurality of channels, performing eigenvalue decomposition on the pilot tone signals on the plurality of channels based on the covariance matrix and determining, as a respiratory feature direction, the direction of an eigenvector with the strongest energy, calculating an angle between the respiratory feature direction and a fixed vector direction, and determining, as the first predetermined number, a minimum experimental value that enables the angle to be stable comprises: A1, acquiring purely respiration-modulated pilot tone signals of N1 points that are received on the plurality of channels; and performing eigenvalue decomposition on the pilot tone signals on the plurality of channels based on the covariance matrix and determining, as a first respiratory feature direction, the direction of an eigenvector with the strongest energy, where N1 is a natural number; A2, calculating an angle $\alpha1$ between the first respiratory feature direction and a fixed vector direction; A3, letting $N_i=N1+\Delta N$, where $\Delta N$ is a natural number; A4, acquiring purely respiration-modulated pilot tone signals of $N_i$ points that are received on the plurality of channels; and performing eigenvalue decomposition on the pilot tone signals on the plurality of channels based on the covariance matrix and determining, as the $i^{th}$ respiratory feature direction, the direction of an eigenvector with the strongest energy; A5, calculating an angle $\alpha_i$ between the $i^{th}$ respiratory feature direction and the fixed vector direction; A6, determining whether a difference between the angle $\alpha1$ and the angle $\alpha_i$ is greater than a predetermined first threshold? if the difference between the angle $\alpha1$ and the angle $\alpha_i$ is greater than the predetermined first threshold, performing step A7; and if the difference between the angle $\alpha1$ and the angle $\alpha_i$ is not greater than the predetermined first threshold, performing step A9; A7, letting $N_{i+1}=N_i+\Delta N$; A8, acquiring purely respiration-modulated pilot tone signals of $N_{i+1}$ points that are received on the plurality of channels; performing eigenvalue decomposition on the pilot tone signals on the plurality of channels based on the covariance matrix and determining, as the $(i+1)^{th}$ respiratory feature direction, the direction of an eigenvector with the strongest energy; calculating an angle $\alpha_{i+1}$ between the $(i+1)^{th}$ respiratory feature direction and the fixed vector direction; determining whether a difference between the angle $\alpha_i$ and the angle $\alpha_{i+1}$ is greater than the predetermined first threshold; if yes, letting $N_i=N_{i+1}$, $\alpha_i=\alpha_{i+1}$, and $N_{i+1}=N_i+\Delta N$, and returning to perform step A8; otherwise, taking $N_i$ as the first predetermined number; A9, letting $N_i=N1$, $\alpha_i=\alpha1$, and $N_{i-1}=N_i-\Delta N$; and A10, acquiring purely respiration-modulated pilot tone signals of $N_{i-1}$ points that are received on the plurality of channels; performing eigenvalue decomposition on the pilot tone signals on the plurality of channels based on the covariance matrix and determining, as the $(i-1)^{th}$ respiratory feature direction, the direction of an eigenvector with the strongest energy; calculating an angle $\alpha_{i-1}$ between the $(i-1)^{th}$ respiratory feature direction and the fixed vector direction; determining whether a difference between the angle $\alpha_i$ and the angle $\alpha_{i-1}$ is not greater than the predetermined first threshold; if yes, letting $N_i=N_{i-1}$, $\alpha_i=\alpha_{i-1}$, and $N_{i-1}=N_i-\Delta N$, and returning to perform step A10; otherwise, taking $N_i$ as the first predetermined number.

In one implementation, the respiratory navigation signal extraction method further comprises: acquiring, for each currently obtained experimental value, distorted pilot tone signals of points with the number being the experimental value that are received on the plurality of channels and generating signal transients when a sequence of RF pulses run; performing eigenvalue decomposition on the distorted pilot tone signals on the plurality of channels based on the covariance matrix and determining, as a distorted feature direction, the direction of an eigenvector with the strongest energy; calculating an angle between the distorted feature direction and a fixed vector direction; and determining, as the second predetermined number, a minimum experimental value that enables the angle to be stable.

In one implementation, said acquiring, for each currently obtained experimental value, distorted pilot tone signals of points with the number being the experimental value that are received on the plurality of channels and generating signal transients when a sequence of RF pulses run, performing eigenvalue decomposition on the distorted pilot tone signals on the plurality of channels based on the covariance matrix and determining, as a distorted feature direction, the direction of an eigenvector with the strongest energy, calculating an angle between the distorted feature direction and a fixed vector direction, and determining, as the second predetermined number, a minimum experimental value that enables the angle to be stable comprises: B1, acquiring distorted pilot tone signals of M1 points that are received on the plurality of channels and generate signal transients when a sequence of RF pulses run; and performing eigenvalue decomposition on the distorted pilot tone signals on the plurality of channels based on the covariance matrix and determining, as a first distorted feature direction, the direction of an eigenvector with the strongest energy, where M1 is a nature number; B2, calculating an angle $\beta1$ between the first distorted feature direction and a fixed vector direction; B3, letting $M_i=M1+\Delta M$, where $\Delta M$ is a natural number; B4, acquiring distorted pilot tone signals of $M_i$ points that are received on the plurality of channels and generate signal transients when the sequence of RF pulses run; and performing eigenvalue decomposition on the distorted pilot tone signals on the plurality of channels based on the covariance matrix and determining, as the $i^{th}$ distorted feature direction, the direction of an eigenvector with the strongest energy; B5, calculating an angle $\beta_i$ between the $i^{th}$ distorted feature direction and the fixed vector direction; B6, determining whether a difference between the angle $\beta1$ and the angle $\beta_i$ is greater than a predetermined second threshold; if the difference between the angle $\beta1$ and the angle $\beta_i$ is greater than the predetermined second threshold, performing step B7; and if the difference between the angle $\beta1$ and the angle $\beta_i$ is not greater than the predetermined second threshold, performing step B9; B7, letting $M_{i+1}=M_i+\Delta M$; B8, acquiring distorted pilot tone signals of $M_{i+1}$ points that are received on the plurality of channels and generating signal transients when the sequence of RF pulses run; performing eigenvalue decomposition on the distorted pilot tone signals on the plurality of channels based on the covariance matrix and determining, as the $(i+1)^{th}$ distorted feature direction, the direction of an eigenvector with the strongest energy; calculating an angle $\beta_{i+1}$ between the $(i+1)^{th}$ distorted feature direction and the fixed vector direction; determining whether a difference between the angle $\beta_i$ and the angle $\beta_{i+1}$ is greater than the predetermined second threshold; if yes, letting $M_i=M_{i+1}$, $\beta_i=\beta_{i+1}$, and $M_{i+1}=M_i+$ ΔN, and returning to perform step B8; otherwise, taking $M_i$ as the second predetermined number; B9, letting $M_i=M1$, $β_i=β1$, and $M_{i-1}=M_i-ΔM$; and B10, acquiring distorted pilot tone signals of $M_{i-1}$ points that are received on the plurality of channels and generate signal transients when the sequence of RF pulses run; performing eigenvalue decomposition on the distorted pilot tone signals on the plurality of channels based on the covariance matrix and determining, as the $(i-1)^{th}$ distorted feature direction, the direction of an eigenvector with the strongest energy; calculating an angle $β_{i-1}$ between the $(i-1)^{th}$ distorted feature direction and the fixed vector direction; determining whether a difference between the angle $β_i$ and the angle $β_{i-1}$ is not greater than the predetermined second threshold; if yes, letting $M_i=M_{i-1}$, $β_i=β_{i-1}$, and $M_{i-1}=M_i-ΔM$, and returning to perform step B10; otherwise, taking $M_i$ as the second predetermined number.

The respiratory navigation signal extraction apparatus provided in the embodiments of the present disclosure comprises: a first determination module configured to acquire purely respiration-modulated pilot tone signals of a first predetermined number of points that are received on a plurality of channels before a sequence of RF pulses run, and perform eigenvalue decomposition on the pilot tone signals on the plurality of channels based on a covariance matrix and determine, as a respiratory feature direction, the direction of an eigenvector with the strongest energy; a second determination module configured to acquire distorted pilot tone signals of a second predetermined number of points that are received on the plurality of channels and generate signal transients when a sequence of RF pulses run, and perform eigenvalue decomposition on the distorted pilot tone signals on the plurality of channels based on the covariance matrix to obtain an eigenvector matrix and determine, as a distorted feature direction, the direction of an eigenvector with the strongest energy; and a signal generation module configured to perform, by using the eigenvector matrix, orthogonal transformation for each of the pilot tone signals received on the plurality of channels, respectively, to obtain a plurality of signals corresponding to the directions of various eigenvectors, and perform, in the respiratory feature direction, projection and addition of other signals in eigenvector directions other than that of a signal in the distorted feature direction, to obtain a respiratory navigation signal.

In one implementation, the second determination module acquires distorted pilot tone signals of the second predetermined number of points that are received on the plurality of channels and generate signal transients when the sequence of RF pulses run for a first cycle.

In one implementation, the respiratory navigation signal extraction apparatus further comprises a third determination module configured to obtain various experimental values by successively increasing or decreasing a first initial experimental value by a predetermined first interval; acquire, for each currently obtained experimental value, purely respiration-modulated pilot tone signals of points with the number being the experimental value that are received on the plurality of channels; perform eigenvalue decomposition on the pilot tone signals on the plurality of channels based on the covariance matrix and determine, as a respiratory feature direction, the direction of an eigenvector with the strongest energy; calculate an angle between the respiratory feature direction and a fixed vector direction; and determine, as the first predetermined number, a minimum experimental value that enables the angle to be stable.

In one implementation, the respiratory navigation signal extraction apparatus further comprises a fourth determination module configured to obtain various experimental values by successively increasing or decreasing a second initial experimental value by a predetermined second interval; acquire, for each currently obtained experimental value, distorted pilot tone signals of points with the number being the experimental value that are received on the plurality of channels and generating signal transients when a sequence of RF pulses run; perform eigenvalue decomposition on the distorted pilot tone signals on the plurality of channels based on the covariance matrix and determine, as a distorted feature direction, the direction of an eigenvector with the strongest energy; calculate an angle between the distorted feature direction and a fixed vector direction; and determine, as the second predetermined number, a minimum experimental value that enables the angle to be stable.

The embodiments of the present disclosure further provide a respiratory navigation signal extraction apparatus, which comprises at least one memory and at least one processor, wherein the at least one memory stores a computer program, and the at least one processor invokes the computer program stored in the at least one memory to carry out the respiratory navigation signal extraction method of any of the above-mentioned implementations.

The magnetic resonance imaging system provided in the embodiments of the present disclosure comprises the respiratory navigation signal extraction apparatus of any of the above-mentioned implementations.

The computer readable storage medium provided in the embodiments of the present disclosure has a computer program stored thereon, wherein the computer program can be executed by a processor to implement the respiratory navigation signal extraction method of any of the above-mentioned implementations.

It can be seen from the above solutions that, in the embodiments of the present disclosure, when the same signal is collected through a plurality of channels, eigenvector decomposition may be performed based on a feature space to find the direction of an eigenvector with the strongest energy, thereby determining a respiratory feature direction of respiratory signals and a distortion feature direction of strongly distorted signals. Then, feature space transformation is performed on each of pilot tone signals received on the plurality of channels, so as to discard signals in the distortion feature direction, and signals in other directions are projected and added in the respiratory feature direction to obtain a respiratory navigation signal used for navigation, thereby achieving de-noising processing.

Further, for the strongly distorted signals, distorted signals during running of a sequence of RF pulses for a first cycle are collected to acquire an eigenvector matrix, so as to perform de-noising processing on subsequently collected signals in a timely manner, thereby obtaining the respiratory navigation signal used for navigation as soon as possible.

Moreover, a first predetermined number that can enable the respiratory feature direction to be stable and a second predetermined number that can enable the distortion feature direction to be stable are predetermined, so that the respiratory navigation signal obtained after the de-noising processing can be more accurate.

In addition, a simple and feasible method for determining the first predetermined number and the second predetermined number is provided, so that the final first predetermined number and second predetermined number can be found regardless of whether an initial experimental point is smaller or larger.

BRIEF DESCRIPTION OF THE DRAWINGS

The above and other features and advantages of the present disclosure will be more apparent to those of ordinary skill in the art from the detailed description of preferred embodiments of the present disclosure with reference to the accompanying drawings, in which.

In the figures, reference numerals are shown as follows.

Figure 1A:
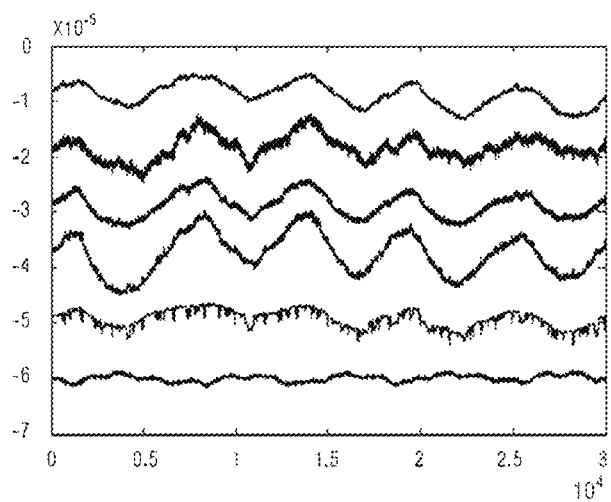
FIG. 1A is a schematic diagram of purely respiration-modulated pilot tone signals received on six channels in one example.
Figure 1B:
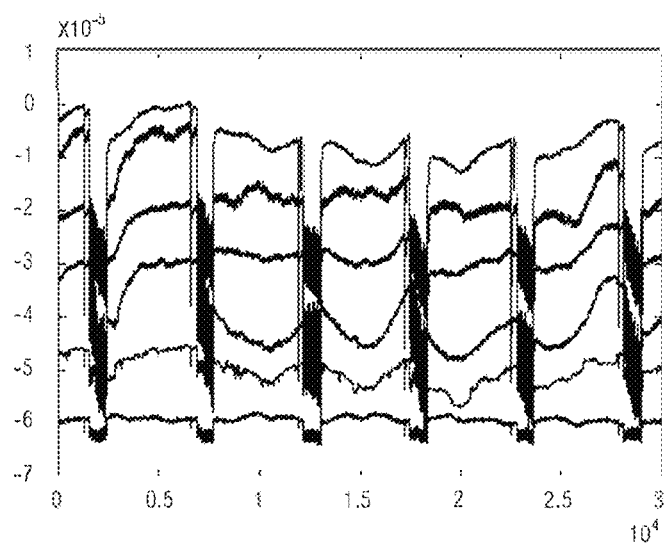
FIG. 1B is a schematic diagram of distorted pilot tone signals during running of a sequence of RF pulses that are received on six channels in one example.

| Reference numerals | Meaning |
| --- | --- |
| S22, S24, S26, S41 to S410, S61 to S610 | Steps |
| S1, S2 | Interval |
| 701 | First determination module |
| 702 | Second determination module |
| 703 | Signal generation module |
| 704 | Third determination module |
| 705 | Fourth determination module |
| 810 | Memory |
| 820 | Processor |

DETAILED DESCRIPTION

In the embodiments of the present disclosure, for the same signal, when a plurality of channels are used to collect the same signal at the same time regardless of whether the signal is a respiratory signal or a strongly distorted signal, signals collected by the plurality of channels must be strongly correlated. From the perspective of matrix analysis, the signals collected by the plurality of channels may constitute an omni-directional feature space, and most of the energy of the signals therein is distributed on one eigenvector. That is, for the respiratory signal, the direction of an eigenvector with the greatest energy is a respiratory feature direction, and for the strongly distorted signal, the direction of an eigenvector with the greatest energy is a distorted feature direction. Therefore, in the embodiments of the present disclosure, feature space transformation may be performed on each of the pilot tone signals received on the plurality of channels, so as to discard signals in the distorted feature direction, and signals in other directions are projected and added in the respiratory feature direction to obtain a respiratory navigation signal used for navigation, thereby achieving de-noising processing.

In order to make the object, technical solutions, and advantages of the present disclosure more apparent, the present disclosure will be described in further detail by way of example embodiments hereinafter.

Figure 2:
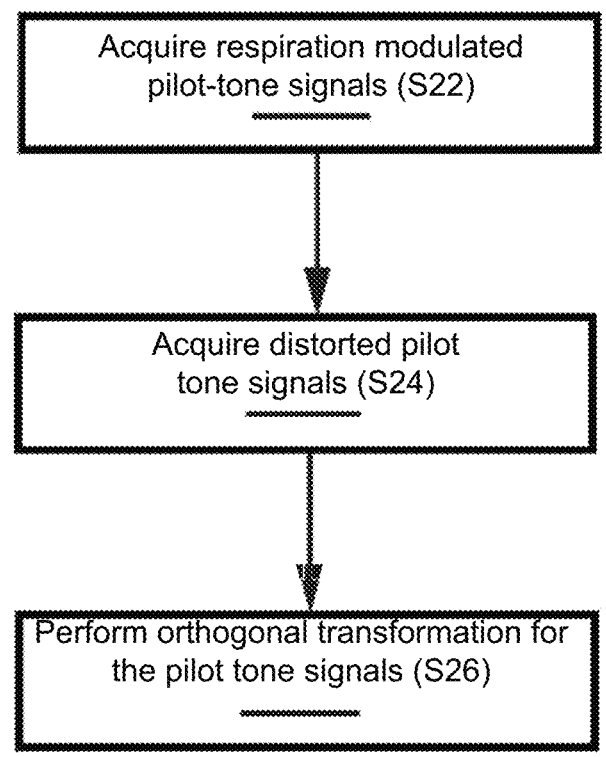
FIG. 2 is an exemplary flow chart of a respiratory navigation signal extraction method in accordance with an embodiment of the present disclosure.
Figure 3A:
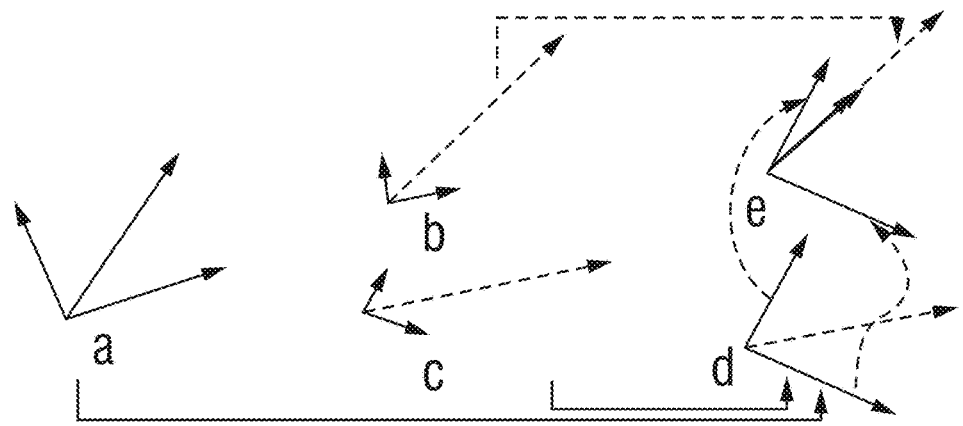
FIG. 3A is an exploded view of assistance in illustrating the method shown in FIG. 2 by taking three channels as an example in accordance with an embodiment of the present disclosure.

FIG. 2 is an exemplary flow chart of a respiratory navigation signal extraction method in an embodiment of the present disclosure. FIG. 3A is an exploded view of assistance in illustrating the method by taking three channels as an example. As shown in FIGS. 2 and 3A, the method may comprise the following steps:

Step S22, acquiring purely respiration-modulated pilot tone signals of a first predetermined number of points (e.g., discrete time sampling points or samples) that are received on a plurality of channels before a sequence of RF pulses run; and performing eigenvalue decomposition on the pilot tone signals on the plurality of channels based on a covariance matrix and determining, as a respiratory feature direction, the direction of an eigenvector with the strongest energy.

For example, after eigenvalue decomposition is performed for purely respiration-modulated pilot tone signals on three channels shown in the diagram a in FIG. 3A, three eigenvector directions shown in the diagram b may be obtained, wherein the longest eigenvector direction shown by a dashed line (that is, the eigenvector direction with the greatest energy) is the respiratory feature direction.

Figure 3B:
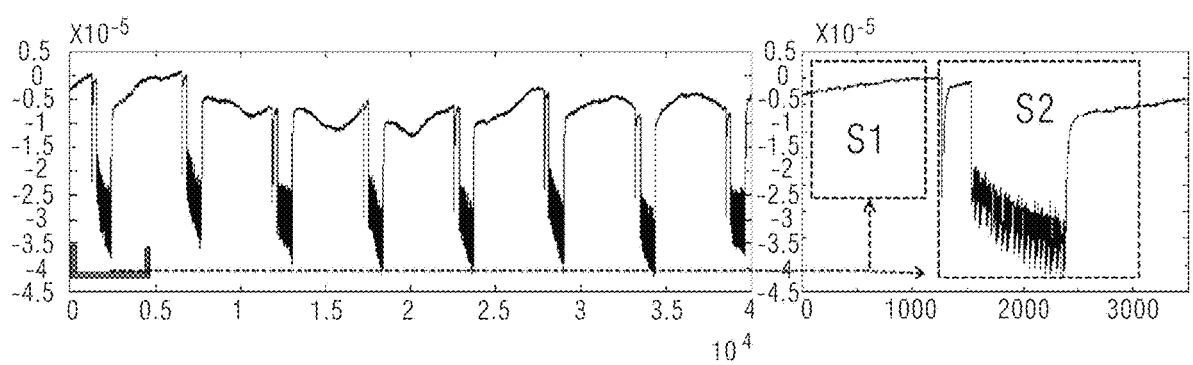
FIG. 3B is a schematic diagram of an example pilot tone signal in accordance with an embodiment of the present disclosure.

In this step, the purely respiration-modulated pilot tone signals before the sequence of RF pulses run may be signals in an interval S1 labeled with a box shown in FIG. 3B. As used herein, the term "run" with respect to the sequence of RF pulses includes the execution, triggering, control, and/or the subsequent transmission of RF pulses for a particular MRI sequence via an MRI apparatus or an appropriate component thereof, as is generally known.

Figure 5:
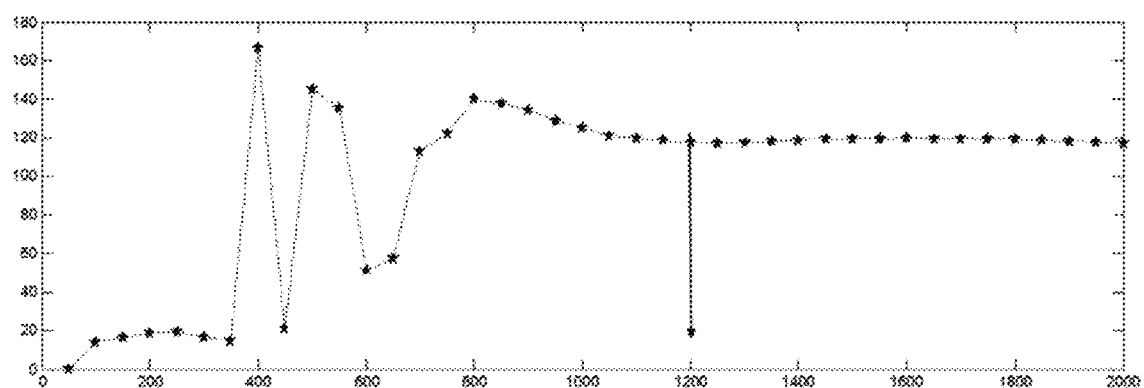
FIG. 5 is a schematic diagram of an example relationship between an experimental value and an angle when determining a first predetermined number by taking six channels in accordance with an embodiment of the present disclosure.

There may be a plurality of methods for determining the first predetermined number, which may, for example, comprise: obtaining various experimental values by successively increasing or decreasing a first initial experimental value by a predetermined first interval; acquiring, for each currently obtained experimental value, purely respiration-modulated pilot tone signals of points with the number being the experimental value that are received on the plurality of channels; performing eigenvalue decomposition on the pilot tone signals on the plurality of channels based on the covariance matrix and determining, as a respiratory feature direction, the direction of an eigenvector with the strongest energy; calculating an angle between the respiratory feature direction and a fixed (e.g. predetermined) vector direction; and determining, as the first predetermined number, a minimum experimental value that enables the angle to be stable. As used herein, the term "stable" with respect to the calculation of the angle includes the angle maintaining a constant or stable value or solution upon the number of points increasing to a particular or predetermined value (e.g., when the number of points increases to 1200 as shown in FIG. 5).

Figure 4:
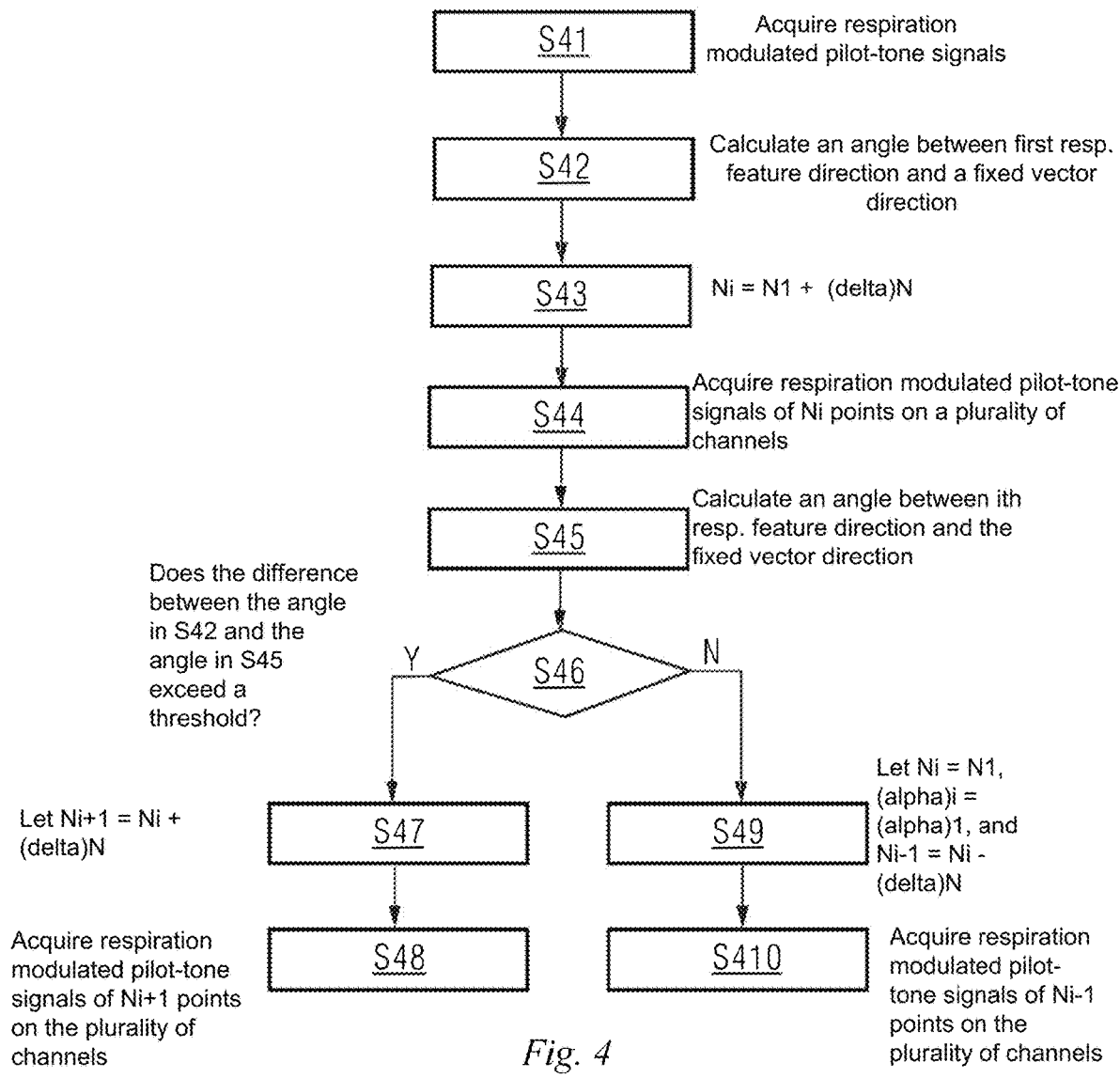
FIG. 4 is a schematic flow chart of a method for determining a first predetermined number in accordance with an embodiment of the present disclosure.

FIG. 4 shows a specific implementation for determining the first predetermined number, and the flow shown in FIG. 4 will be described below in detail.

Step S24, acquiring distorted pilot tone signals of a second predetermined number of points that are received on the plurality of channels and generating signal transients when a sequence of RF pulses run, and performing eigenvalue decomposition on the distorted pilot tone signals on the plurality of channels based on the covariance matrix to obtain an eigenvector matrix and determining, as a distorted feature direction, the direction of an eigenvector with the strongest energy. As used herein, the term "transient" with respect to signals may include a signal having a sudden change in a value or state as understood in the art. For example, a transient signal may include "spikes," or sudden deviations exceeding a threshold signal amplitude or value that occurs within a time span that is less than a threshold time period.

For example, after eigenvalue decomposition is performed for distorted pilot tone signals during running of the sequence of RF pulses that are of the three channels shown in the diagram a in FIG. 3A, three eigenvector directions shown in the diagram c may be obtained, wherein the longest eigenvector direction shown by a dashed line (that is, the eigenvector direction with the greatest energy) is the distorted feature direction.

In this step, distorted pilot tone signals of the second predetermined number of points that are received on the plurality of channels and generate signal transients when the sequence of RF pulses run for a first (e.g., an initial) cycle may be acquired. For example, the distorted pilot tone signals may be signals in an interval S2 labeled with a box shown in FIG. 3B.

In this way, step S26 may be performed for all subsequent pilot tone signals by using the eigenvector matrix calculated when the sequence of RF pulses run for the first cycle. Certainly, in actual applications, it can also be other cycles of a sequence of pulses, for example, a second cycle of the sequence of pulses. Because after eigenvector matrix calculation is performed based on the first sequences of RF pulses and the processing in step S26 is performed for all the subsequent pilot tone signals, a respiratory navigation signal that can be used for navigation can be obtained as soon as possible.

There may also be a plurality of methods for determining the second predetermined number, which may, for example, comprise: obtaining various experimental values by successively increasing or decreasing a second initial experimental value by a predetermined second interval; acquiring, for each currently obtained experimental value, distorted pilot tone signals of points with the number being the experimental value that are received on the plurality of channels and generating signal transients when a sequence of RF pulses run; performing eigenvalue decomposition on the distorted pilot tone signals on the plurality of channels based on the covariance matrix and determining, as a distorted feature direction, the direction of an eigenvector with the strongest energy; calculating an angle between the distorted feature direction and a fixed vector direction; and determining, as the second predetermined number, a minimum experimental value that enables the angle to be stable.

Figure 6:
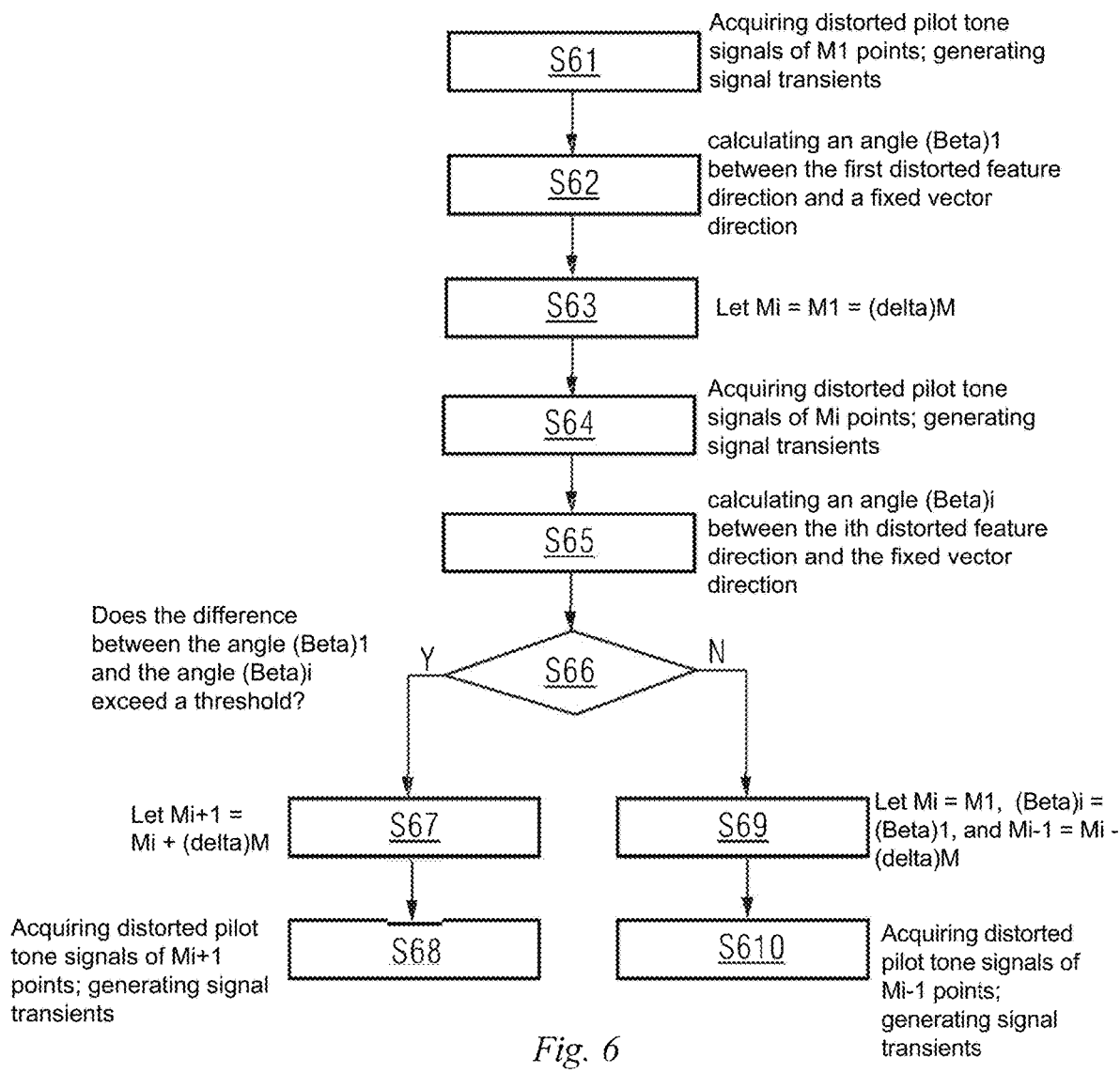
FIG. 6 is a schematic flow chart of a method for determining a second predetermined number in accordance with an embodiment of the present disclosure.

FIG. 6 shows a specific implementation for determining the second predetermined number, and the flow shown in FIG. 6 will be described below in detail.

Step S26, performing, by using the eigenvector matrix, orthogonal transformation for each of the pilot tone signals received on the plurality of channels to obtain a plurality of signals corresponding to the directions of various eigenvectors; and performing, in the respiratory feature direction, projection and addition of signals in eigenvector directions other than that of a signal in the distorted feature direction, to obtain a respiratory navigation signal For example, after orthogonal transformation is performed, by using the eigenvector matrix, on each of pilot tone signals received on the three channels shown in the diagram a in FIG. 3A, signals in the three feature directions shown in the diagram c can also be obtained. In this case, a signal in the distorted feature direction may be discarded as shown in the diagram d, and projection and addition are performed, in the respiratory feature direction shown in the diagram b, on signals in remaining two feature directions as shown in the diagram e, so as to obtain a respiratory navigation signal.

FIG. 4 is a schematic flow chart of a method for determining a first predetermined number in an embodiment of the present disclosure. As shown in FIG. 4, the method may comprise the following steps:

S41, acquiring purely respiration-modulated pilot tone signals of N1 points that are received on the plurality of channels; and performing eigenvalue decomposition on the pilot tone signals on the plurality of channels based on the covariance matrix and determining, as a first respiratory feature direction, the direction of an eigenvector with the strongest energy, where N1 is a natural number.

S42, calculating an angle α1 between the first respiratory feature direction and a fixed vector direction.

S43, letting $N_i = N1 + \Delta N$, wherein $\Delta N$ is a natural number.

S44, acquiring purely respiration-modulated pilot tone signals of $N_i$ points that are received on the plurality of channels; and performing eigenvalue decomposition on the pilot tone signals on the plurality of channels based on the covariance matrix and determining, as the $i^{th}$ respiratory feature direction, the direction of an eigenvector with the strongest energy.

S45, calculating an angle $\alpha_i$ between the $i^{th}$ respiratory feature direction and the fixed vector direction.

S46, determining whether a difference between the angle α1 and the angle $\alpha_i$ is greater than a predetermined first threshold. If the difference between the angle α1 and the angle $\alpha_i$ is greater than the predetermined first threshold, performing step S47; and if the difference between the angle α1 and the angle $\alpha_i$ is not greater than the predetermined first threshold, performing step S49.

In this step, the first threshold may be predetermined to be very small according to the actual situations, so as to ensure the stability of the angle.

S47, letting $N_{i+1} = N_i + \Delta N$.

S48, acquiring purely respiration-modulated pilot tone signals of $N_{i+1}$ points that are received on the plurality of channels; performing eigenvalue decomposition on the pilot tone signals on the plurality of channels based on the covariance matrix and determining, as the $(i+1)^{th}$ respiratory feature direction, the direction of an eigenvector with the strongest energy; calculating an angle $\alpha_{i+1}$ between the $(i+1)^{th}$ respiratory feature direction and the fixed vector direction; determining whether a difference between the angle $\alpha_i$ and the angle $\alpha_{i+1}$ is greater than the predetermined first threshold; if yes, letting $N_i = N_{i+1}$, $\alpha_i = \alpha_{i+1}$, and $N_{i+1} = N_i + \Delta N$, and returning to perform step S48; otherwise, taking $N_i$ as the first predetermined number.

S49, letting $N_i = N1$, $\alpha_i = \alpha 1$, and $N_{i-1} = N_i - \Delta N$.

S410, acquiring purely respiration-modulated pilot tone signals of $N_{i-1}$ points that are received on the plurality of channels; performing eigenvalue decomposition on the pilot tone signals on the plurality of channels based on the covariance matrix and determining, as the $(i-1)^{th}$ respiratory feature direction, the direction of an eigenvector with the strongest energy; calculating an angle $\alpha_{i-1}$ between the $(i-1)^{th}$ respiratory feature direction and the fixed vector direction; determining whether a difference between the angle $\alpha_i$ and the angle $\alpha_{i-1}$ is not greater than the predetermined first threshold; if yes, letting $N_i=N_{i-1}$, $\alpha_i=\alpha_{i-1}$, and $N_{i-1}=N_i-\Delta N$, and returning to perform step S410; otherwise, taking $N_i$ as the first predetermined number.

FIG. 5 shows a schematic diagram of a relationship between an angle and an experimental value that is calculated by taking six channels as an example in one embodiment of the present disclosure. As shown in FIG. 5, horizontal coordinates are number values, and vertical coordinates are angles between respiratory feature directions and a fixed vector direction. It can be seen that, in this example, from the beginning of an initial experimental value of 50, i.e., N1=50, the first predetermined interval is 50, i.e., $\Delta N$=50, and the angle is found to be stable when the calculation goes to point 1200. This process may be implemented by performing steps S41 to S48. In FIG. 5, the calculation continues to 2000 to verify accuracy of 1200.

In other implementations, for the example shown in FIG. 5, if the initial value is 1500, 1200 may be found by performing steps S41 to S46 and S49 to S410.

FIG. 6 is a schematic flow chart of a method for determining a second predetermined number in an embodiment of the present disclosure. As shown in FIG. 6, the method may comprise the following steps:

S61, acquiring distorted pilot tone signals of M1 points that are received on the plurality of channels and generating signal transients when a sequence of RF pulses run; and performing eigenvalue decomposition on the distorted pilot tone signals on the plurality of channels based on the covariance matrix and determining, as a first distorted feature direction, the direction of an eigenvector with the strongest energy, where M1 is a natural number.

S62, calculating an angle $\beta 1$ between the first distorted feature direction and a fixed vector direction.

S63, letting $M_i=M1+\Delta M$, where $\Delta M$ is a natural number.

S64, acquiring distorted pilot tone signals of $M_i$ points that are received on the plurality of channels and generating signal transients when the sequence of RF pulses run; and performing eigenvalue decomposition on the distorted pilot tone signals on the plurality of channels based on the covariance matrix and determining, as the $i^{th}$ distorted feature direction, the direction of an eigenvector with the strongest energy.

S65, calculating an angle $\beta_i$ between the $i^{th}$ distorted feature direction and the fixed vector direction.

S66, determining whether a difference between the angle $\beta_1$ and the angle $\beta_i$ is greater than a predetermined second threshold. If the difference between the angle $\beta_1$ and the angle $\beta_i$ is greater than the predetermined second threshold, performing S67; and if the difference between the angle $\beta_1$ and the angle $\beta_i$ is not greater than the predetermined second threshold, performing S69.

In this step, the second threshold may be predetermined to be very small according to the actual situations, so as to ensure the stability of the angle.

S67, letting $M_{i+1}=M_i+\Delta M$.

S68, acquiring distorted pilot tone signals of $M_{i+1}$ points that are received on the plurality of channels and generating signal transients when the sequence of RF pulses run; performing eigenvalue decomposition on the distorted pilot tone signals on the plurality of channels based on the covariance matrix and determining, as the $(i+1)^{th}$ distorted feature direction, the direction of an eigenvector with the strongest energy; calculating an angle $\beta_{i+1}$ between the $(i+1)^{th}$ distorted feature direction and the fixed vector direction; determining whether a difference between the angle $\beta_i$ and the angle $\beta_{i+1}$ is greater than the predetermined second threshold; if yes, letting $M_i=M_{i+1}$, $\beta_i=\beta_{i+1}$, and $M_{i+1}=M_i+\Delta_N$, and returning to perform step S68; otherwise, taking $M_i$ as the second predetermined number.

S69, letting $M_i=M1$, $\beta_i=\beta 1$, and $M_{i-1}=M_i-\Delta M$.

S610, acquiring distorted pilot tone signals of $M_{i-1}$ points that are received on the plurality of channels and generating signal transients when the sequence of RF pulses run; performing eigenvalue decomposition on the distorted pilot tone signals on the plurality of channels based on the covariance matrix and determining, as the $(i-1)^{th}$ distorted feature direction, the direction of an eigenvector with the strongest energy; calculating an angle $\beta_{i-1}$ between the $(i-1)^{th}$ distorted feature direction and the fixed vector direction; determining whether a difference between the angle $\beta_i$ and the angle $\beta_{i-1}$ is not greater than the predetermined second threshold; if yes, letting $M_i=M_{i-1}$, $\beta_i=\beta_{i-1}$, and $M_{i-1}=M_i-\Delta M$, and returning to perform step S610; otherwise, taking $M_i$ as the second predetermined number.

The respiratory navigation signal extraction method in the embodiments of the present disclosure has been described in detail above, and then the respiratory navigation signal extraction apparatus in the embodiments of the present disclosure will be described in detail below. For the parts which are not disclosed in the apparatus embodiment of the present disclosure, reference may be made to corresponding descriptions in the method embodiment of the present disclosure, which will not be repeatedly described herein.

Figure 7:
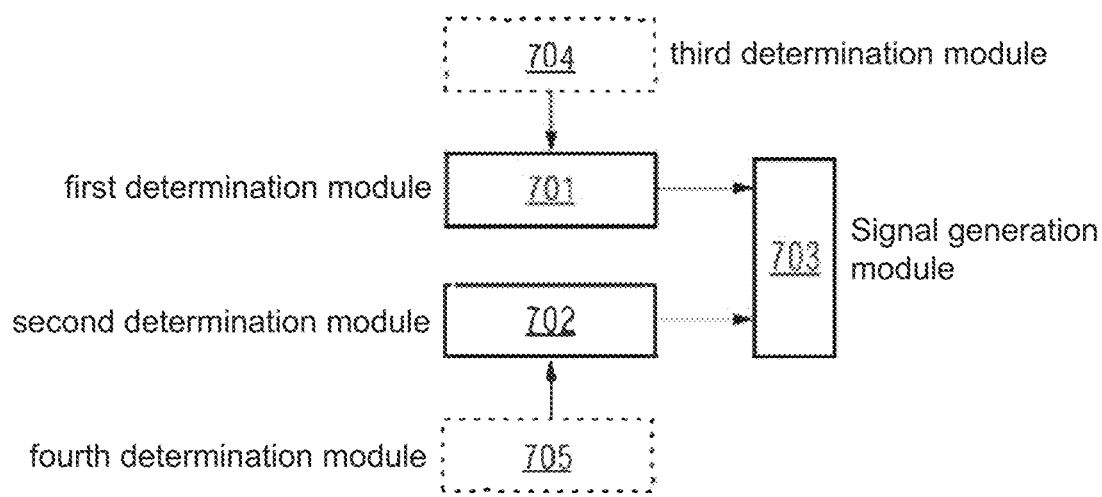
FIG. 7 is an exemplary structural diagram of a respiratory navigation signal extraction apparatus in accordance with an embodiment of the present disclosure.

FIG. 7 is an exemplary structural diagram of a respiratory navigation signal extraction apparatus in an embodiment of the present disclosure. As shown by the solid-line portion in FIG. 7, the apparatus may comprise a first determination module 701, a second determination module 702, and a signal generation module 703. Each of the determination modules 701, 702, 703, etc., may be implemented as any suitable number and type of processors, processing circuitry (e.g. a CPU, a processing unit/module, an ASIC, a logic module or a programmable gate array, etc.), software, or combinations thereof. The determination modules may be alternatively be referred to as "circuits," "circuitry," or "units" instead of "modules."

The first determination module 701 is configured to acquire purely respiration-modulated pilot tone signals of a first predetermined number of points that are received on a plurality of channels before a sequence of RF pulses run, and perform eigenvalue decomposition on the pilot tone signals on the plurality of channels based on a covariance matrix and determine, as a respiratory feature direction, the direction of an eigenvector with the strongest energy.

The second determination module 702 is configured to acquire distorted pilot tone signals of a second predetermined number of points that are received on the plurality of channels and generate signal transients when a sequence of RF pulses run, and perform eigenvalue decomposition on the distorted pilot tone signals on the plurality of channels based on the covariance matrix to obtain an eigenvector matrix and determine, as a distorted feature direction, the direction of an eigenvector with the strongest energy. In specific implementation, the second determination module 702 may acquire distorted pilot tone signals of the second predetermined number of points that are received on the plurality of channels and generate signal transients when the sequence of RF pulses run for a first cycle, so as to perform an eigenvalue decomposition operation.

The signal generation module 703 is configured to perform, by using the eigenvector matrix, orthogonal transformation for each of the pilot tone signals received on the plurality of channels, respectively, to obtain a plurality of signals corresponding to the directions of various eigenvectors, and perform, in the respiratory feature direction, projection and addition of signals in eigenvector directions other than that of a signal in the distorted feature direction, to obtain a respiratory navigation signal.

In one implementation, as shown by the dashed-line portion in FIG. 7, the apparatus may further comprise a third determination module 704 configured to obtain various experimental values by successively increasing or decreasing a first initial experimental value by a predetermined first interval; acquire, for each currently obtained experimental value, purely respiration-modulated pilot tone signals of points with the number being the experimental value that are received on the plurality of channels; perform eigenvalue decomposition on the pilot tone signals on the plurality of channels based on the covariance matrix and determine, as a respiratory feature direction, the direction of an eigenvector with the strongest energy; calculate an angle between the respiratory feature direction and a fixed vector direction; and determine, as the first predetermined number, a minimum experimental value that enables the angle to be stable.

Figure 8:
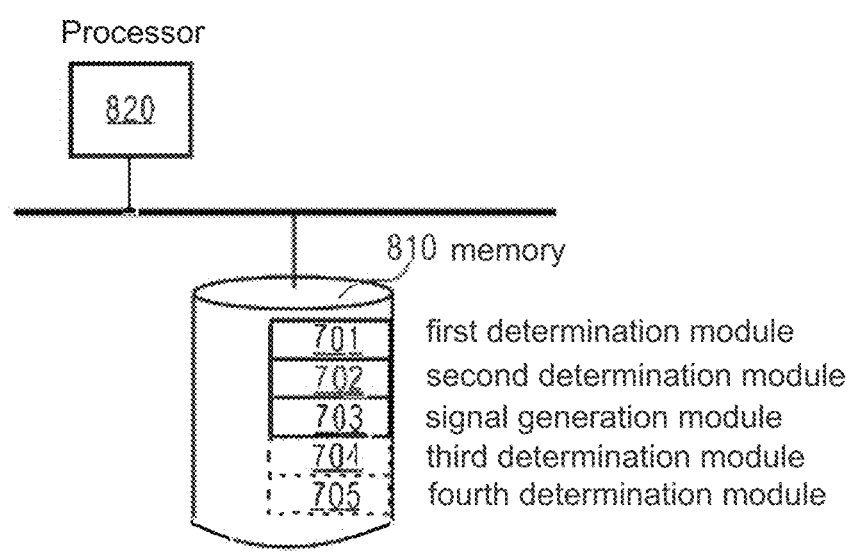
FIG. 8 is an exemplary structural diagram of another respiratory navigation signal extraction apparatus in accordance with an embodiment of the present disclosure.

In one implementation, as shown by the dashed-line portion in FIG. 7, the apparatus may further comprise a fourth determination module 705 configured to obtain various experimental values by successively increasing or decreasing a second initial experimental value by a predetermined second interval; acquire, for each currently obtained experimental value, distorted pilot tone signals of points with the number being the experimental value that are received on the plurality of channels and generate signal transients when a sequence of RF pulses run; perform eigenvalue decomposition on the distorted pilot tone signals on the plurality of channels based on the covariance matrix and determine, as a distorted feature direction, the direction of an eigenvector with the strongest energy; calculate an angle between the distorted feature direction and a fixed vector direction; and determine, as the second predetermined number, a minimum experimental value that enables the angle to be stable, FIG. 8 is an exemplary structural diagram of another respiratory navigation signal extraction apparatus in an embodiment of the present disclosure. As shown in FIG. 8, the respiratory navigation signal extraction apparatus may comprise at least one memory 810 and at least one processor 820. Certainly, the respiratory navigation signal extraction apparatus may further comprise some other components such as a communication port. These components can communicate via a bus.

The at least one memory 810 is configured to store a computer program. In one implementation, the computer program may be understood as comprising modules of the respiratory navigation signal extraction apparatus shown in FIG. 7, that is, the first determination module 701, the second determination module 702, the signal generation module 703, and even the third module 704 and the fourth module 705.

Moreover, the at least one memory 810 may further store an operating system and the like. The operating system may include but is not limited to an Android operating system, a Symbian operating system, a Windows operating system, a Linux operating system, and the like.

The at least one processor 820 is configured to invoke the computer program stored in the at least one memory 810 (e.g., a noon-transitory computer-readable medium) to carry out the respiratory navigation signal extraction method in the embodiments of the present disclosure based on a function of receiving data through at least one port. The processor 820 may be a CPU, a processing unit/module, an ASIC, a logic module or a programmable gate array, or the like.

It needs to be noted that not all the steps and modules in the flows and structural diagrams described above are necessary, and some steps or modules may be omitted or modified according to practical requirements and the particular application. The execution order of the various steps is not fixed and may be adjusted according to requirements. The division of various modules is merely function division adopted for ease of description. In actual implementation, one module may be implemented by a plurality of modules, respectively, and functions of a plurality of modules may also be implemented by the same module. These modules may be located in the same device, or may be located in different devices.

Hardware modules in various implementations may be implemented mechanically or electrically. For example, one hardware module may comprise a specifically designed permanent circuit or logic device (e.g. a dedicated processor, such as an FPGA or an ASIC) for accomplishing specific operations. The hardware module may also comprise a programmable logic device or circuit (e.g., including a general-purpose processor or other programmable processors), which is configured temporarily by software, for performing specific operations. Whether the hardware module is implemented in a mechanical manner, by using a dedicated permanent circuit or by using a temporarily configured circuit (e.g. configured by software) may be decided according to costs and time.

The magnetic resonance imaging system provided in the embodiments of the present disclosure may comprise the respiratory navigation signal extraction apparatus of any of the above-mentioned implementations.

The present disclosure further provides a non-transitory machine-readable storage medium storing instructions used for enabling a machine to carry out the method in the present application. Specifically, a system or apparatus with a storage medium may be provided, and software program codes for implementing the functions of any of the above-mentioned implementations are stored on the storage medium, and a computer (or CPU or MPU) of the system or apparatus is caused to read out and execute the program codes stored in the storage medium. Moreover, an operating system operating on a computer may be caused to accomplish some or all of the actual operations based on an instruction of the program codes. The program codes read out from the storage medium may be further written into a memory provided in an expansion board inserted into the computer or written into a memory provided in an expansion unit connected to the computer, then a CPU and the like installed on the expansion board or the expansion unit is caused to execute some or all of the actual operations based on an instruction of the program codes, thereby implementing the functions of any of the above-mentioned implementations. The implementations of the storage medium for providing the program codes comprise a floppy disk, a hard disk, a magnetic optical disc, an optical disc (e.g., CD-ROM, CD-R, CD-RW, DVD-ROM, DVD-RAM, DVD-RW and DVD+RW), a magnetic tape, a non-volatile memory card and an ROM. Optionally, the program codes may be downloaded from a server computer via a communication network.

Implementation effects of the technical solution in the embodiments of the present disclosure will be verified by experiments below.

FIGS. 9 to 12 respectively show an effect view of respiratory navigation signals extracted in different application scenarios by taking four channels as an example. In FIGS. 9 to 12, the first four rows are pilot tone signals received on four channels respectively, and the fifth row is an extracted respiratory navigation signal.

Figure 9:
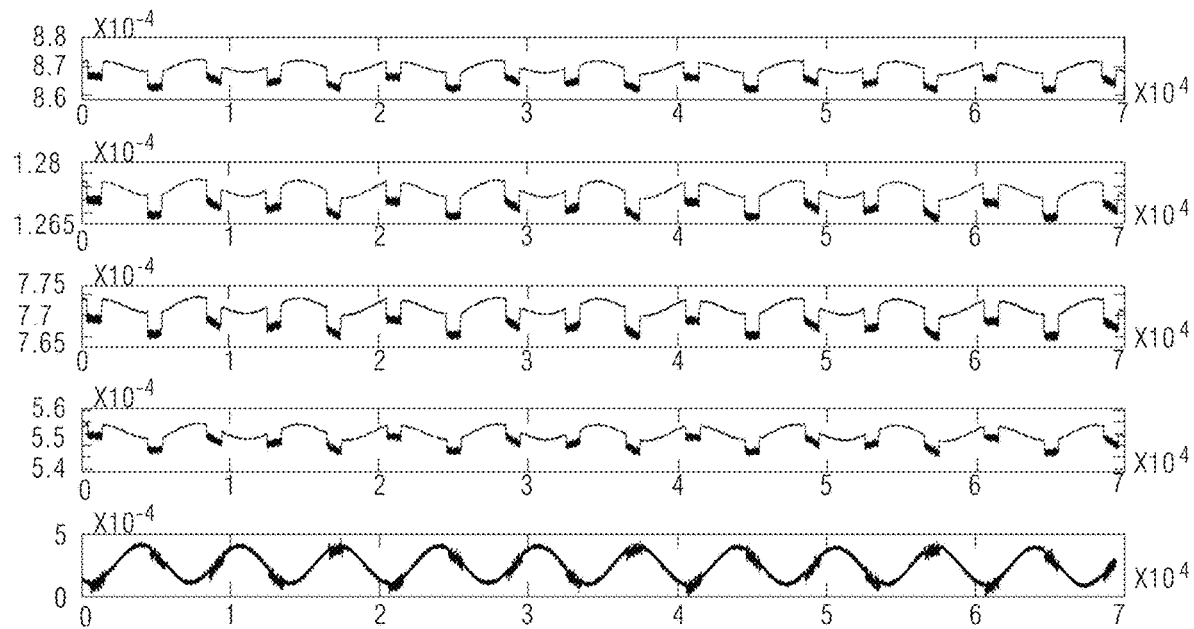
FIGS. 9 to 12 respectively show an example effect view of respiratory navigation signals extracted in different application scenarios using four channels in accordance with an embodiment of the present disclosure.
Figure 10:
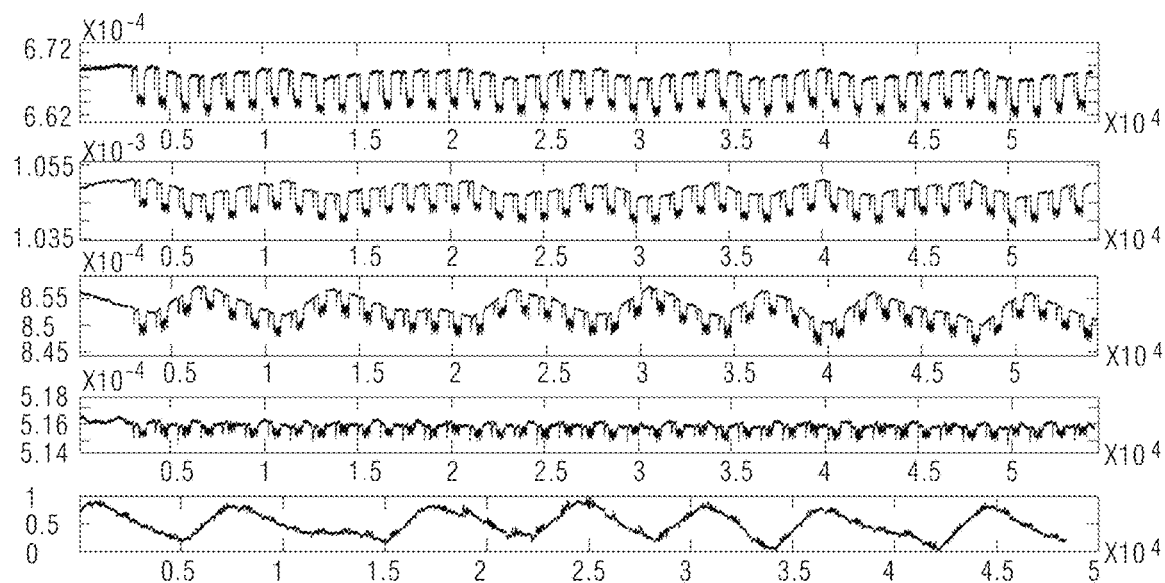
Figure 11:
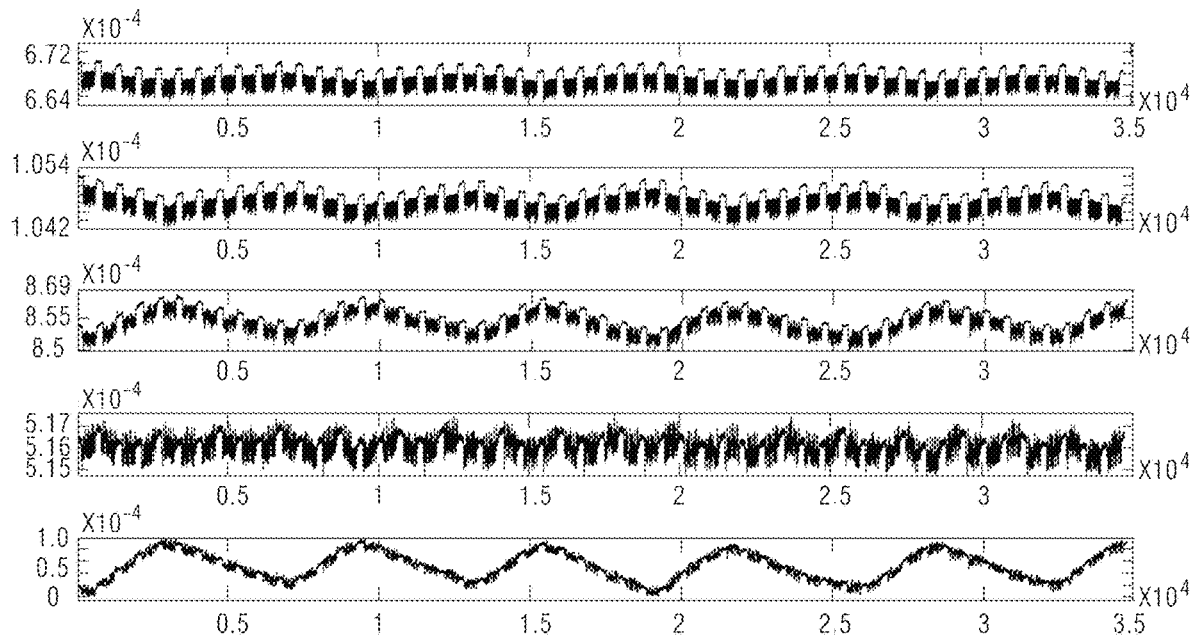
Figure 12:
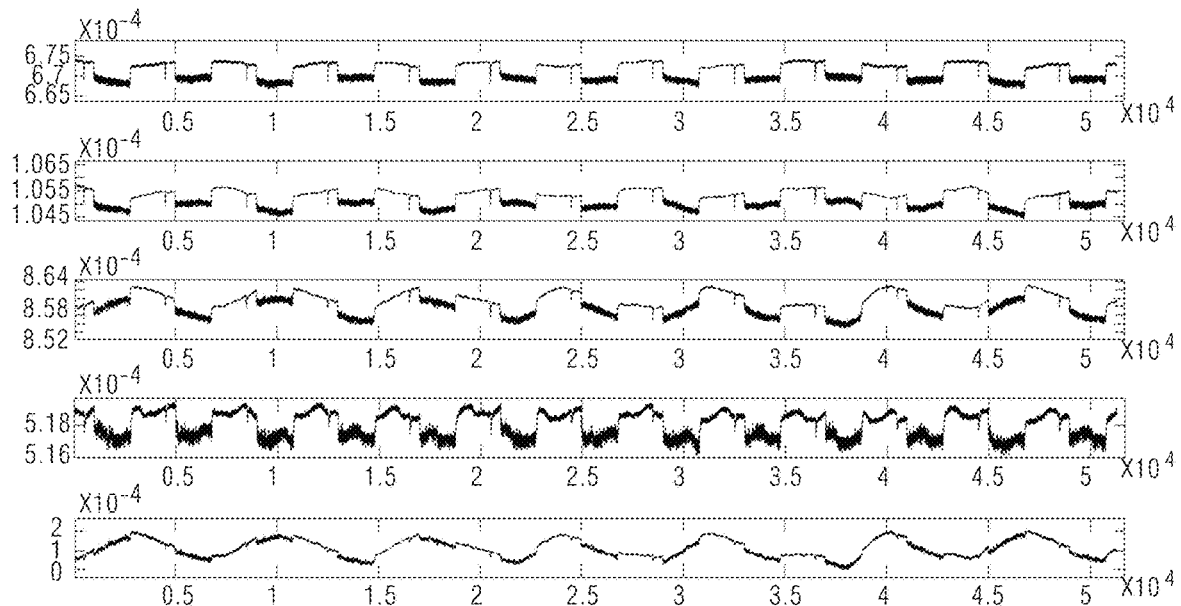

FIG. 9 is a respiratory navigation signal extraction result based on pulse distorted data and simulated respiratory motion, FIG. 10 is a respiratory navigation signal extraction result based on a TSE blade sequence of RF pulses and real volunteer data, FIG. 11 is a respiratory navigation signal extraction result quickly acquired based on real volunteer data, and FIG. 12 is a respiratory navigation signal extraction result of a turbo flash based on real volunteer data.

It can be seen that a good respiratory navigation signal that can be used for scanning navigation is obtained regardless of an application scenario.

It can be seen from the above solutions that, in the embodiments of the present disclosure, when the same signal is collected through a plurality of channels, eigenvector decomposition may be performed based on a feature space to find the direction of an eigenvector with the strongest energy, thereby determining a respiratory feature direction of respiratory signals and a distorted feature direction of strongly distorted signals. Then, feature space transformation is performed on each of pilot tone signals received on the plurality of channels, so as to discard signals in the distorted feature direction, and signals in other directions are projected and added in the respiratory feature direction to obtain a respiratory navigation signal used for navigation, thereby achieving de-noising processing.

Further, for the strongly distorted signals, distorted signals during running of a sequence of RF pulses for a first cycle are collected to acquire an eigenvector matrix, so as to perform de-noising processing on subsequently collected signals in a timely manner, thereby obtaining the respiratory navigation signal used for navigation as soon as possible. Once obtained in the manner, the respiratory navigation signal may be used for navigation as part of a magnetic resonance imaging procedure.

Moreover, a first predetermined number that can enable the respiratory feature direction to be stable and a second predetermined number that can enable the distorted feature direction to be stable are predetermined, so that the respiratory navigation signal obtained after the de-noising processing can be more accurate.

In addition, a simple and feasible method for determining the first predetermined number and the second predetermined number is provided, so that the final first predetermined number and second predetermined number can be found regardless of whether an initial experimental point is smaller or larger.

The above descriptions are merely preferred embodiments of the present disclosure but not intended to limit the present disclosure, and any modifications, equivalent replacements, improvements, etc. made within the spirit and principle of the present disclosure should be included within the scope of protection of the present disclosure.

The invention claimed is:

1. A respiratory navigation signal extraction method, comprising:

acquiring, from a plurality of channels prior to execution of a transmitted sequence of radio frequency (RF) pulses via a magnetic resonance imaging (MRI) apparatus, respiration-modulated pilot tone signals having a first predetermined number of samples;

determining, as a respiratory feature direction, a direction of a first eigenvector having the greatest energy by performing an eigenvalue decomposition on the pilot tone signals using a covariance matrix;

acquiring, via the plurality of channels, distorted pilot tone signals having a second predetermined number of samples, the distorted pilot tone signals including transients caused by execution of the transmitted sequence of RF pulses;

determining, as a distortion feature direction, a direction of a second eigenvector having the greatest energy by performing an eigenvalue decomposition on the disturbed pilot tone signals using the covariance matrix to obtain an eigenvector matrix;

performing, for each of the pilot tone signals received on the plurality of channels, respectively, an orthogonal transformation using the eigenvector matrix to obtain a plurality of signals corresponding to directions of a set of eigenvectors;

performing, in the respiratory feature direction, projection and addition of signals from among the plurality of signals in eigenvector directions other than that of a signal in the distortion feature direction to obtain a respiratory navigation signal; and using the obtained respiratory navigation signal for navigation as part of a magnetic resonance imaging procedure.

2. The respiratory navigation signal extraction method of claim 1, wherein acquiring the distorted pilot tone signals comprises:

acquiring the distorted pilot tone signals when the transmitted sequence of RF pulses is executed as an initial cycle.

3. The respiratory navigation signal extraction method of claim 1, further comprising:

calculating an angle between the respiratory feature direction and a predetermined vector direction; and determining, as the first predetermined number of samples, a minimum value that enables the angle to maintain a constant value.

4. The respiratory navigation signal extraction method of claim 3, wherein the determination of the minimum value that enables the angle to maintain a constant value comprises:

acquiring the respiration-modulated pilot tone signals having a predetermined number of samples equal to N1, with N1 being a natural number;

determining, as an initial respiratory feature direction, a direction of an eigenvector having a greatest energy by performing eigenvalue decomposition of the pilot tone signals using the covariance matrix; and calculating the angle $\alpha 1$ between the initial respiratory feature direction and the predetermined vector direction;

setting a value $N_i = N1 + \Delta N$, with $\Delta N$ being a natural number;

acquiring, via the plurality of channels, respiration-modulated pilot tone signals having a number of samples equal to $N_i$;

determining, as an $i^{th}$ respiratory feature direction, a direction of an eigenvector having a greatest energy by performing eigenvalue decomposition of the pilot tone signals using the covariance matrix and;

calculating an angle $\alpha_i$ between the $i^{th}$ respiratory feature direction and the predetermined vector direction;

when a difference between the angle $\alpha 1$ and the angle $\alpha_i$ is greater than a predetermined first threshold, setting $N_{i+1}=N_i+\Delta N$, and when the difference between the angle $\alpha 1$ and the angle $\alpha_i$ is not greater than the predetermined first threshold, setting $N_i=N1$, $\alpha_i=\alpha 1$, and $N_{i-1}=N_i-\Delta N$;

acquiring, via the plurality of channels, respiration-modulated pilot tone signals having a number of samples equal to $N_{i+1}$;

iteratively performing eigenvalue decomposition of the pilot tone signals using the covariance matrix and determining, as an $(i+1)^{th}$ respiratory feature direction, a direction of an eigenvector having the greatest energy;

iteratively calculating an angle $\alpha_{i+1}$ between the $(i+1)^{th}$ respiratory feature direction and the predetermined vector direction;

when a difference between the angle $\alpha_i$ and the angle $\alpha_{i+1}$ is greater than the predetermined first threshold, setting $N_i=N_{i+1}$, $\alpha_i=\alpha_{i+1}$, and $N_{i+1}=N_i+\Delta N$, and repeating the acquiring, via the plurality of channels, of the respiration-modulated pilot tone signals having a number of samples equal to $N_{i+1}$;

when a difference between the angle $\alpha_i$ and the angle $\alpha_{i+1}$ is not greater than the predetermined first threshold, setting $N_i=N_{i+1}$, $\alpha_i=\alpha_{i+1}$, and $N_{i+1}=N_i+\Delta N$, repeating the acquiring, via the plurality of channels, of the respiration-modulated pilot tone signals having a number of samples equal to $N_{i+1}$, and setting $N_i$ as the first predetermined number of samples;

acquiring, via the plurality of channels, respiration-modulated pilot tone signals having a number of samples equal to $N_{i-1}$;

performing eigenvalue decomposition of the pilot tone signals on the plurality of channels using the covariance matrix to determine, as an $(i-1)^{th}$ respiratory feature direction, a direction of an eigenvector having the strongest energy;

calculating an angle $\alpha_{i-1}$ between the $(i-1)^{th}$ respiratory feature direction and the predetermined vector direction;

when a difference between the angle $\alpha_i$ and the angle $\alpha_{i-1}$ is not greater than the predetermined first threshold, then setting $N_i=N_{i-1}$, $\alpha_i=\alpha_{i-1}$, and $N_{i-1}=N_i-\Delta N$, and repeating the acquiring, via the plurality of channels, of the respiration-modulated pilot tone signals having a number of samples equal to $N_{i+1}$;

when a difference between the angle $\alpha_i$ and the angle $\alpha_{i-1}$ is greater than the predetermined first threshold, then setting $N_i$ as the first predetermined number of samples.

5. The respiratory navigation signal extraction method of claim 1, further comprising:

calculating an angle between the distorted feature direction and a predetermined vector direction; and determining, as the second predetermined number of samples, a minimum value that enables the angle to maintain a constant value.

6. The respiratory navigation signal extraction method of claim 5, wherein determining, as the second predetermined number of samples, a minimum value that enables the angle to maintain a constant value comprises:

acquiring distorted pilot tone signals having a predetermined number of samples equal to M1, with M1 being a natural number;

determining, as an initial distorted feature direction, the direction of an eigenvector with a greatest energy by performing eigenvalue decomposition on the distorted pilot tone signals using the covariance matrix;

calculating an angle $\beta 1$ between the initial distorted feature direction and a predetermined vector direction;

setting a value $M_i=M1+\Delta M$, with $\Delta M$ being a natural number;

acquiring, via the plurality of channels, distorted pilot tone signals having a number of samples equal to $M_i$; and determining, as an $i^{th}$ distortion feature direction, a direction of an eigenvector having a greatest energy by performing eigenvalue decomposition of the disturbed pilot tone signals using the covariance matrix;

calculating an angle $\beta_i$ between the $i^{th}$ distortion feature direction and the predetermined vector direction (S65);

when a difference between the angle $\beta 1$ and the angle $\beta_i$ is greater than a predetermined second threshold, setting $M_{i+1}=M_i+\Delta M$, and when the difference between the angle $\beta 1$ and the angle $\beta_i$ is not greater than the predetermined second threshold, setting $M_i=M1$, $\beta_i=\beta 1$, and $M_{i-1}=M_i-\Delta M$;

acquiring distorted pilot tone signals having a number of samples equal to $M_{i+1}$;

iteratively performing eigenvalue decomposition on the distorted pilot tone signals using the covariance matrix and determining, as the $(i+1)^{th}$ distortion feature direction, a direction of an eigenvector having the strongest energy;

iteratively calculating an angle $\beta_{i+1}$ between the $(i+1)^{th}$ distortion feature direction and the predetermined vector direction;

when a difference between the angle $\beta_i$ and the angle $\beta_{i+1}$ is greater than the predetermined second threshold, setting $M_i=M_{i+1}$, $\beta_i=\beta_{i+1}$, and $M_{i+1}=M_i+\Delta N$, and repeating the acquiring, via the plurality of channels, of the distorted pilot tone signals having a number of samples equal to $M_{i+1}$, and when a difference between the angle $\beta_i$ and the angle $\beta_{i+1}$ is not greater than the predetermined second threshold, setting $M_i$ as the second predetermined number, and acquiring, via the plurality of channels, distorted pilot tone signals having a number of samples equal to $M_{i-1}$;

performing eigenvalue decomposition on the distorted pilot tone signals on the plurality of channels using the covariance matrix to determine, as an $(i-1)^{th}$ distortion feature direction, a direction of an eigenvector having a greatest energy;

calculating an angle $\beta_{i-1}$ between the $(i-1)^{th}$ distortion feature direction and the predetermined vector direction;

when a difference between the angle $\beta_i$ and the angle $\beta_{i-1}$ is not greater than the predetermined second threshold, setting $M_i=M_{i-1}$, $\beta_i=\beta_{i-1}$, and $M_{i-1}=M_i-\Delta M$, and repeating the acquiring, via the plurality of channels, of the distorted pilot tone signals having a number of samples equal to $M_{i-1}$, and when a difference between the angle $\beta_i$ and the angle $\beta_{i-1}$ is greater than the predetermined second threshold, setting $M_i$ as the second predetermined number of samples.

7. A respiratory navigation signal extraction apparatus, comprising:
a memory; and
one or more processors configured to execute machine-readable instructions stored in the memory to:
acquire, from a plurality of channels prior to execution of a transmitted sequence of radio frequency (RF) pulses via a magnetic resonance imaging (MRI) apparatus, respiration-modulated pilot tone signals having a first predetermined number of samples;
determine, as a respiratory feature direction, a direction of a first eigenvector having the greatest energy by performing an eigenvalue decomposition on the pilot tone signals using a covariance matrix;
acquire, via the plurality of channels, distorted pilot tone signals having a second predetermined number of samples, the distorted pilot tone signals including transients caused by execution of the transmitted sequence of RF pulses;
determine, as a distortion feature direction, a direction of a second eigenvector having the greatest energy by performing an eigenvalue decomposition on the disturbed pilot tone signals using the covariance matrix to obtain an eigenvector matrix;
perform, for each of the pilot tone signals received on the plurality of channels, respectively, an orthogonal transformation using the eigenvector matrix to obtain a plurality of signals corresponding to directions of a set of eigenvectors;
perform, in the respiratory feature direction, projection and addition of signals from among the plurality of signals in eigenvector directions other than that of a signal in the distortion feature direction to obtain a respiratory navigation signal; and
use the obtained respiratory navigation signal for navigation as part of a magnetic resonance imaging procedure.

8. The respiratory navigation signal extraction apparatus of claim 7, wherein the one or more processors are configured to acquire the distorted pilot tone signals when the transmitted sequence of RF pulses is executed as an initial cycle.

9. The respiratory navigation signal extraction apparatus of claim 7, wherein the one or more processors are configured to:
obtain a set of test values by successively increasing or decreasing a first initial test value by a predetermined first interval;
acquire, via the plurality of channels for each currently obtained test value, respiration-modulated pilot tone signals having a number of samples equal to the respective test value;
perform eigenvalue decomposition of the pilot tone signals on the plurality of channels using the covariance matrix to determine a direction of an eigenvector having a greatest energy as a respiratory feature direction;
calculate an angle between the respiratory feature direction and a predetermined vector direction; and
determine, as the first predetermined number of samples, a minimum experimental value that enables the angle to maintain a constant value.

10. The respiratory navigation signal extraction apparatus of claim 9, wherein the one or more processors are configured to:
obtain another set of test values by successively increasing or decreasing a second initial test value by a predetermined second interval;
acquire, via the plurality of channels for each currently obtained test value, distorted pilot tone signals of points having a number of samples equal to the respective test value;
perform eigenvalue decomposition of the distorted pilot tone signals on the plurality of channels using the covariance matrix to determine a direction of an eigenvector having a greatest energy as a distortion feature direction;
calculate an angle between the distortion feature direction and a predetermined vector direction; and
determine, as the second predetermined number of samples, a minimum experimental value that enables the angle to maintain a constant value.

11. A non-transitory computer readable storage medium having a computer program stored thereon that, when executed by one or more processors, cause the one or more processors to:
acquire, from a plurality of channels prior to execution of a transmitted sequence of radio frequency (RF) pulses via a magnetic resonance imaging (MRI) apparatus, respiration-modulated pilot tone signals having a first predetermined number of samples;
determine, as a respiratory feature direction, a direction of a first eigenvector having the greatest energy by performing an eigenvalue decomposition on the pilot tone signals using a covariance matrix;
acquire, via the plurality of channels, distorted pilot tone signals having a second predetermined number of samples, the distorted pilot tone signals including transients caused by execution of the transmitted sequence of RF pulses;
determine, as a distortion feature direction, a direction of a second eigenvector having the greatest energy by performing an eigenvalue decomposition on the disturbed pilot tone signals using the covariance matrix to obtain an eigenvector matrix;
perform, for each of the pilot tone signals received on the plurality of channels, respectively, an orthogonal transformation using the eigenvector matrix to obtain a plurality of signals corresponding to directions of a set of eigenvectors;
perform, in the respiratory feature direction, projection and addition of signals from among the plurality of signals in eigenvector directions other than that of a signal in the distortion feature direction to obtain a respiratory navigation signal; and
use the obtained respiratory navigation signal for navigation as part of a magnetic resonance imaging procedure.

* * * * *